US009642545B2

(12) United States Patent
Yoon et al.

(10) Patent No.: US 9,642,545 B2
(45) Date of Patent: *May 9, 2017

(54) NEURAL PROBE WITH OPTICAL STIMULATION CAPABILITY

(71) Applicant: The Regents of the University of Michigan, Ann Arbor, MI (US)

(72) Inventors: Euisik Yoon, Superior Township, MI (US); Il-Joo Cho, Seoul (KR)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 15/012,334

(22) Filed: Feb. 1, 2016

(65) Prior Publication Data

US 2016/0143551 A1    May 26, 2016

Related U.S. Application Data

(63) Continuation of application No. 13/510,822, filed as application No. PCT/US2010/057377 on Nov. 19, 2010, now Pat. No. 9,247,889.

(Continued)

(51) Int. Cl.
*A61B 5/04* (2006.01)
*A61N 5/06* (2006.01)
(Continued)

(52) U.S. Cl.
CPC ........ *A61B 5/04001* (2013.01); *A61B 5/0048* (2013.01); *A61N 5/0601* (2013.01);
(Continued)

(58) Field of Classification Search
CPC  A61B 5/04001; A61N 1/0529; A61N 1/0531; A61N 1/0534; A61N 5/0622
See application file for complete search history.

(56) References Cited

U.S. PATENT DOCUMENTS 8,355,768 B2 * 1/2013 Masmanidis ...... A61B 5/04001
                                                                600/372
9,247,889 B2 * 2/2016 Yoon ................. A61B 5/04001
(Continued)

FOREIGN PATENT DOCUMENTS

JP    2003255235 A    9/2003

OTHER PUBLICATIONS

International Search Report for PCT/US2010/057377, dated Aug. 2, 2011, 3 pages.

*Primary Examiner* — Lee S Cohen
(74) *Attorney, Agent, or Firm* — Reising Ethington P.C.

(57) ABSTRACT

A neural probe is disclosed for optically stimulating or silencing neurons and recording electrical responses to the stimulus. Using patterning techniques, an integral optical waveguide may be fabricated on the probe for transmitting neuron-affecting light from a light source to a probe tip. The probe tip may include one or more electrodes to receive electrical responses from stimulated neurons for recording or further processing. According to various embodiments, the disclosed neural probes may utilize multiple light sources simultaneously, switch between multiple light sources, or utilize a single light source to stimulate or silence multiple neuron locations simultaneously via multiple probe tips or via multiple light-emitting sites located along the length of the probe. Neural probes are thereby provided that have sufficient spatial resolution to accurately target, stimulate, and record the reaction of neurons, or as few as a single neuron, utilizing a slim, compact structure.

23 Claims, 5 Drawing Sheets

Related U.S. Application Data

(60) Provisional application No. 61/262,765, filed on Nov. 19, 2009.

(51) Int. Cl.
    *A61B 5/00*    (2006.01)
    *A61N 1/05*    (2006.01)

(52) U.S. Cl.
    CPC .......... *A61N 5/0622* (2013.01); *A61N 1/0529* (2013.01); *A61N 1/0551* (2013.01); *A61N 2005/063* (2013.01); *A61N 2005/0612* (2013.01); *A61N 2005/0651* (2013.01); *A61N 2005/0653* (2013.01)

(56) References Cited

U.S. PATENT DOCUMENTS

| | | | |
|---|---|---|---|
| 2002/0028990 A1* | 3/2002 | Shepherd | A61B 5/14552 600/340 |
| 2005/0216072 A1 | 9/2005 | Mahadevan-Jansen et al. | |
| 2006/0155348 A1 | 7/2006 | deCharms | |
| 2006/0282014 A1* | 12/2006 | Kipke | A61B 5/04001 600/573 |
| 2008/0177363 A1* | 7/2008 | Schouenborg | A61N 1/0529 607/116 |
| 2008/0255439 A1* | 10/2008 | Tang | A61B 5/04001 600/373 |
| 2009/0069871 A1 | 3/2009 | Mahadevan-Jansen et al. | |
| 2011/0087311 A1* | 4/2011 | Zorzos | A61N 5/0601 607/89 |
| 2011/0112591 A1* | 5/2011 | Seymour | A61B 5/0084 607/3 |

* cited by examiner

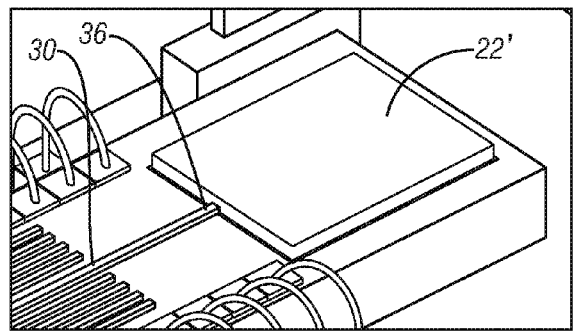
FIG. 4
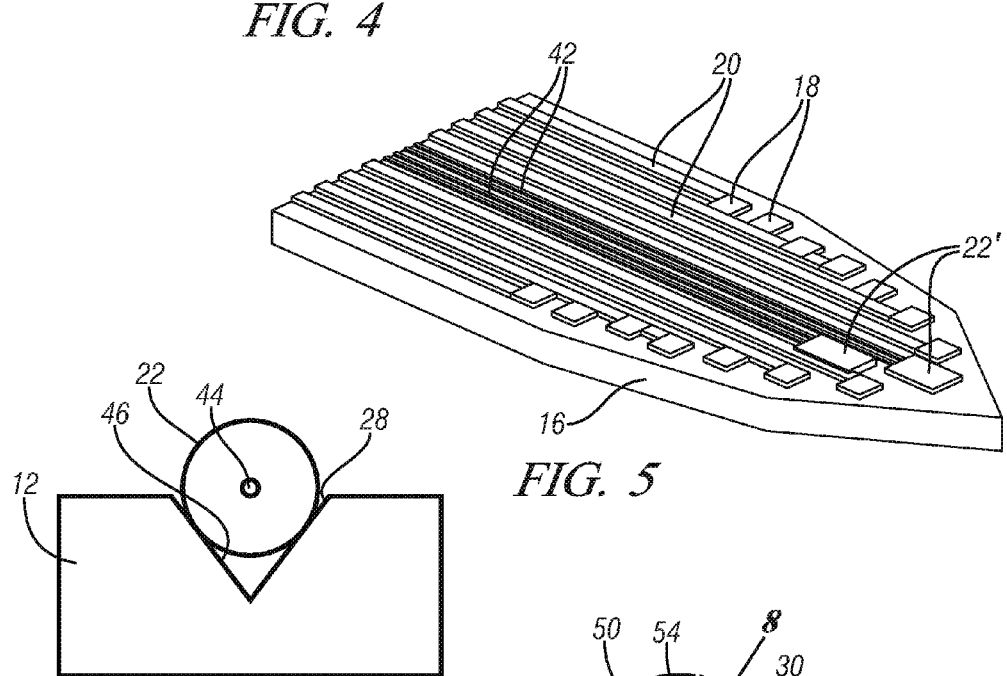
FIG. 5
FIG. 6
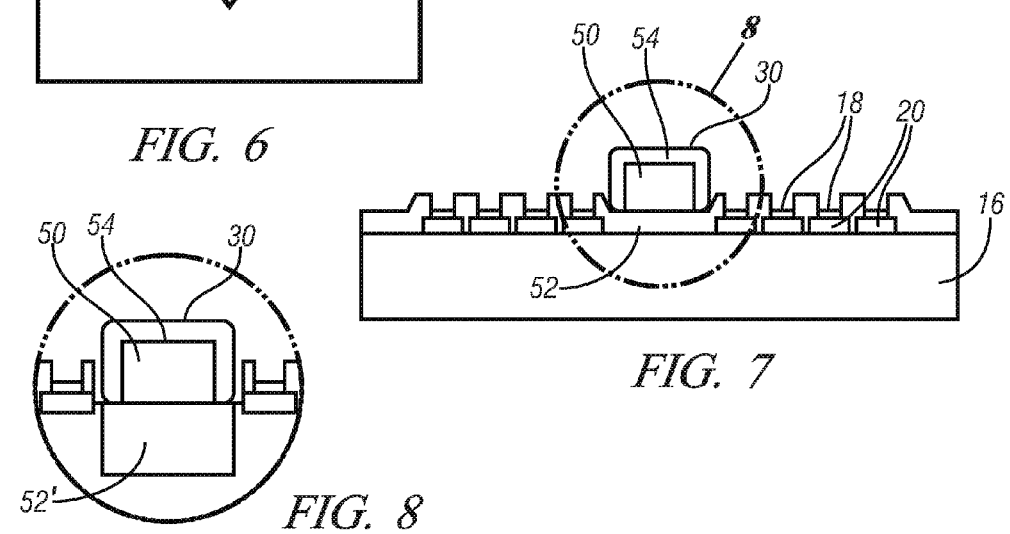
FIG. 7
FIG. 8

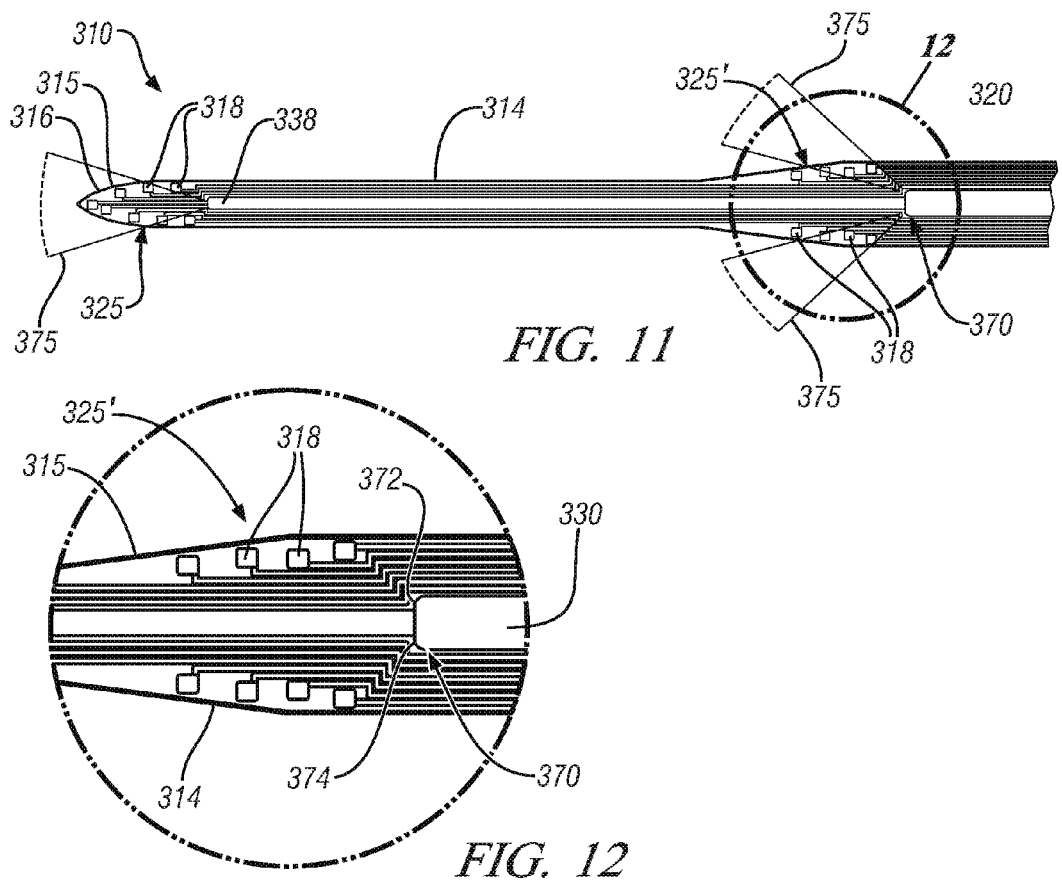
FIG. 11
FIG. 12
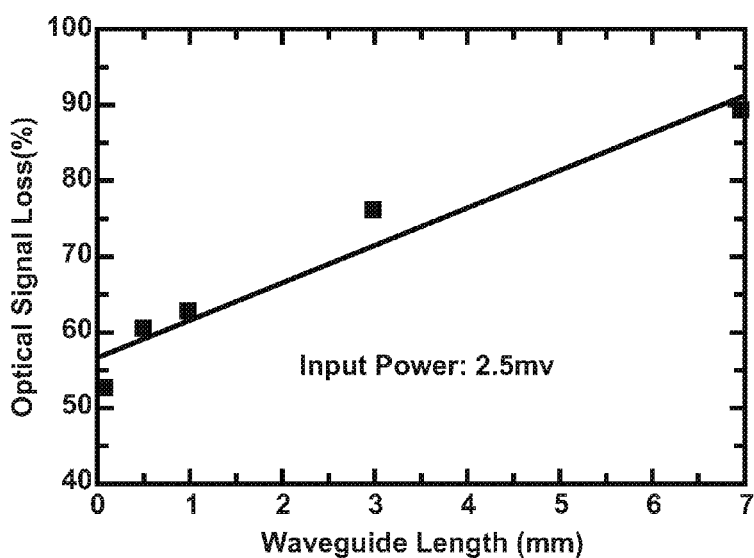
FIG. 14

NEURAL PROBE WITH OPTICAL STIMULATION CAPABILITY

CROSS-REFERENCE TO RELATED APPLICATIONS

This application is a continuation of U.S. application Ser. No. 13/510,822 filed on Nov. 19, 2010, now U.S. Pat. No. 9,247,889, which claims the benefit of U.S. Provisional Application No. 61/262,765 filed on Nov. 18, 2009. The entire contents of these prior applications are hereby incorporated by reference.

STATEMENT OF FEDERALLY-SPONSORED RESEARCH

This invention was made with government support under EEC9986866 awarded by the National Science Foundation. The government has certain rights in the invention.

TECHNICAL FIELD

This invention relates generally to neural probes and, more particularly, to optical neural probes for accurately stimulating and/or recording electrical responses of neurons.

BACKGROUND OF THE INVENTION

Massively-parallel access to the activity of large populations of individual neurons with high spatial and temporal resolution has been a long-sought goal in neuroscience. With advances in MEMS and microelectronics, there has been significant progress toward this goal as planar fabrication processes have been applied to realize chronic extracellular microelectrode arrays. Many previously reported neural probes use electrical signals to stimulate neurons. However, such electrical stimulation can damage neurons. Additionally, because the necessary electrical fields extend across large areas rather than individual neurons, such electrical stimulation can also suffer from poor spatial resolution. To address these problems, an optical stimulation method has been attempted with some success using an optical fiber attached to a probe shank as the optical source (S. Royer et al., "Recording and stimulation of single neurons in the hippocampus of the behaving rat," Society for Neuroscience Annual Meeting, 2008). However, this hybrid structure makes the probe bulky because the size of the optical fiber is comparable to the size of the probe. Also, the hybrid structure is difficult to be accurately assembled and this structure makes it difficult to control the target stimulation position.

SUMMARY OF THE INVENTION

According to one embodiment, there is provided a neural probe that includes a probe body, a shank extending from the probe body to a tip, a light-emitting diode (LED) light source attached to the tip for providing neuron-affecting light at the tip, and one or more recording electrodes attached to the tip for receiving electrical responses to the neuron-affecting light.

According to another embodiment, there is provided a neural probe that includes a probe body, a shank extending from the probe body to a tip, a light-emitting diode (LED) light source patterned on the shank for providing neuron-affecting light, and one or more recording electrodes attached to the tip for receiving electrical responses to the neuron-affecting light.

According to another embodiment, there is provided a neural probe that includes a probe body, a shank extending from the probe body to a tip and having an outer perimeter, a light-emitting diode (LED) light source patterned at the tip for providing neuron-affecting light at the tip, and a plurality of recording electrodes for receiving electrical responses to the neuron-affecting light, wherein the plurality of recording electrodes are attached to the tip such that they are closer to the outer perimeter of the shank than the LED light source.

BRIEF DESCRIPTION OF THE DRAWINGS

Preferred exemplary embodiments of the invention will hereinafter be described in conjunction with the appended drawings, wherein like designations denote like elements, and wherein:

FIG. 4 is a partial view of an exemplary neural probe including an edge-emitting LED light source;

FIG. 5 is a perspective view of a neural probe tip including LED light sources mounted on the tip;

FIG. 6 is a cross-sectional view through the probe body and fiber optic of the exemplary neural probe of FIG. 1;

FIG. 7 is a cross-sectional view through the tip of the exemplary neural probe of FIG. 1;

FIG. 8 is a partial view of FIG. 7 showing an alternative embodiment of a waveguide cladding layer;

FIG. 11 is a top view of a neural probe shank including multiple electrode array regions;

FIG. 12 is an enlarged view of a portion of FIG. 11, showing a light emitting junction;

FIG. 14 is a plot of optical signal loss per waveguide unit length for an exemplary neural probe.

DETAILED DESCRIPTION OF THE PREFERRED EMBODIMENTS

Described below are exemplary embodiments of an optical neural probe that may have sufficient spatial resolution to accurately target, stimulate, and record the reaction of neurons, or as few as a single neuron, utilizing a slim, compact structure. In general, the disclosed embodiments of the optical neural probe utilize structures that emit neuron-affecting light to selectively target neurons and that include recording electrodes near the region of light emission to receive any electrical responses from the targeted neuron or neurons and transmit the responses to a location to be recorded or processed. The neuron-affecting light can be used to stimulate or silence individual or groups of neurons. Such light can include visible and/or non-visible light. Stimulation or silencing of multiple sites is made possible by certain variations of the disclosed probe, as well as stimulation or silencing by more than one wavelength of light either simultaneously or sequentially. Although the following description at times refers to light stimulation of neurons and sites, without specifically mentioning the use of light to silence neurons, it will be appreciated by those skilled in the art that the light can be used for either or both purposes, depending on such things as the wavelength and intensity of the emitted light.

Figure 1:
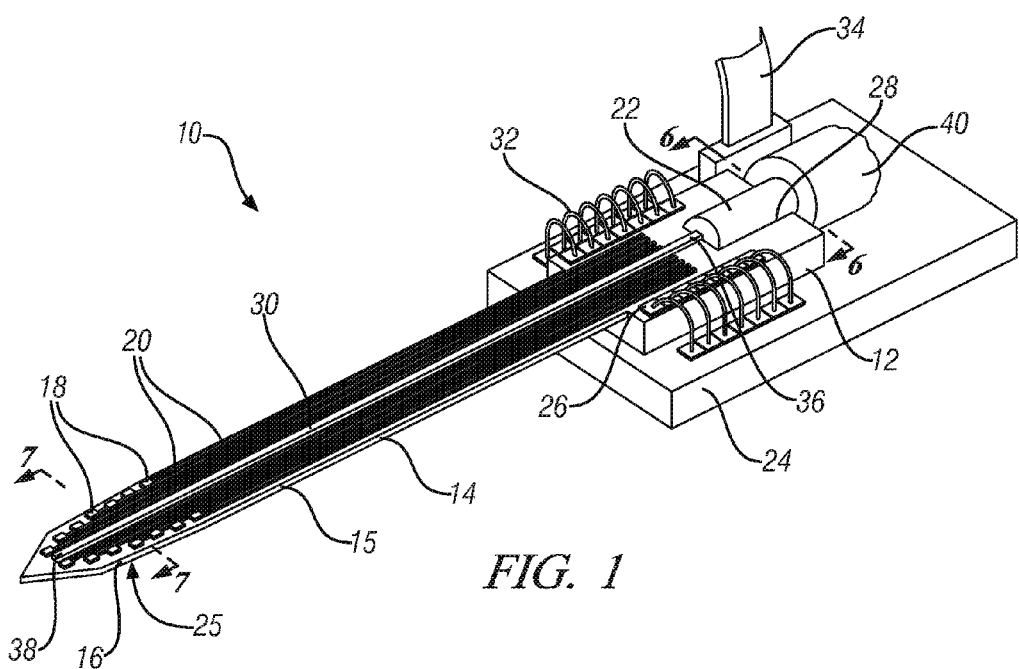
FIG. 1 is an exemplary neural probe including an optical waveguide and a fiber optic light source.

Referring to FIG. 1, a neural probe 10 is shown, according to one embodiment. The exemplary neural probe includes a probe body 12, a shank 14 extending from the probe body 12 to a tip 16, one or more recording electrodes 18, electrode leads 20, and a light source 22 for emitting neuron-affecting light at the tip 16. As shown in FIG. 1, probe 10 may be attached to and/or supported by a printed circuit board (PCB) 24. Probe body 12 generally serves as the portion of the probe from which shank 14 extends and where various probe electrical connections are located. It may be constructed from a heavily boron doped single crystal silicon. In this embodiment, probe body 12 and shank 14 are integral—i.e., formed together as one piece. Probe body 12 includes electrical connections 26, which may be gold pads or another electrically conductive material, for electrical communication with PCB 24 and/or some other component. Probe body 12 may also include a groove 28 for supporting and positioning light source 22, as will be discussed in more detail below.

Shank 14 has an outer perimeter 15 and extends from the probe body 12 to the tip 16 and supports electrodes 18 and electrode leads 20. It should be noted that FIG. 1 is not necessarily to scale. For example, shank 14 may appear needle-like in shape when viewed actual size, with tip 16 at the point of the needle-like shape. In one embodiment, the shank 14 can extend from about 1-7 mm, preferably about 5 mm, in length from the probe body. The shank has a width transverse to the length ranging from 50-150 μm, and a thickness from about 10-20 μm. Of course, these are only exemplary ranges, and several factors may be considered when selecting the dimensions of the shank 14, such as strength, desired depth of probing, and the number of electrodes 18 desired, to name a few. In this embodiment, shank 14 also supports a portion of an optical waveguide 30, as will be discussed below.

Tip 16 is at the end of shank 14 furthest from the probe body 12 and is pointed in this embodiment. Recording electrodes 18 are located and attached to tip 16 and may be arranged in an array generally positioned about the perimeter or edge of the tip 16. The electrodes 18 can receive electrical responses from neurons when stimulated by the emitted light. In some embodiments, electrodes 18 may be located elsewhere, along the shank 14, for example, where neuron-affecting light may be emitted. The electrodes 18 may be iridium electrodes, or they can be constructed from other suitable materials with low impedance, such as iridium oxide, other metals, or carbon nanotubes, for example.

Electrode leads 20 extend along shank 14 to electrically connect each electrode to the probe body 12. Though not explicitly shown in FIG. 1, each lead 20 may be electrically connected to one of the connections 26 at the probe body for communication with PCB 24, where provided, or other components or devices. Leads 20 may be about 0.5 μm thick (raised from the surface of the shank) and range from about 2-5 μm wide. Electrode leads 20 transmit electrical responses received by electrodes 18 from stimulated neurons to the probe body 12. The electrical responses can be sent through electrical connections 26 to PCB 24, where provided, for processing there or at another location external to the PCB. For example, as shown in FIG. 1, conductive bonding wires 32 can provide electrical connections between the probe 10 and the PCB. The PCB 24 can communicate through a cable 34, as shown, or through other means, with a computer, controller, data-logger, or other equipment. Alternatively, or in addition to connection to an external controller, a controller or control circuit may be integrated with the probe 10 by mounting the controller directly on the probe body 12 for massively parallel access.

Light source 22 provides neuron-affecting light for emission near recording electrodes 18, in this case at tip 16. In this embodiment, light source 22 is a fiber optic light source. Fiber optic light source 22 works together with optical waveguide 30 to emit light near recording electrodes 18. The embodiment shown in FIG. 1 includes an integrated optical waveguide 30 extending along the length of the shank 14 from the probe body 12 to the tip 16. The optical waveguide 30 is supported by and attached to the shank 14. The waveguide 30 abuts the fiber optic light source 22 at a source end 36 and extends to the tip 16 at an emitting end 38. The fiber optic may be coupled to an external light source (not shown) to deliver light to the optical waveguide and may also include one or more cladding layers 40. In the embodiment shown in FIG. 1, the emitting end 38 of waveguide 30 lies near the end of tip 16 to provide light at the end of the tip. However, end 38 may alternatively lie within an electrode array region 25, or the waveguide 30 may extend along shank 14 from the probe body 12 such that it does not extend into the electrode array region, so long as the light intensity is sufficient to stimulate neurons near the electrodes 18 from emitting end 38.

Figure 2:
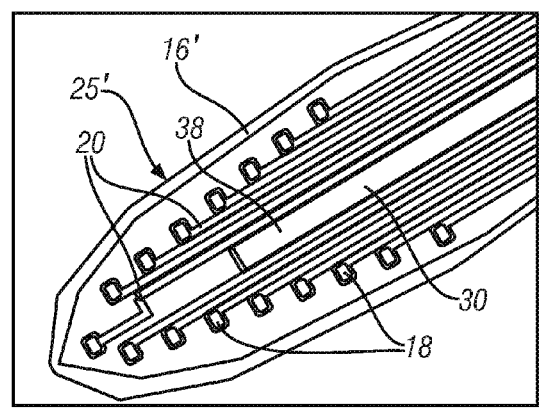
FIG. 2 is a top view of a neural probe tip according to one embodiment.
Figure 3:
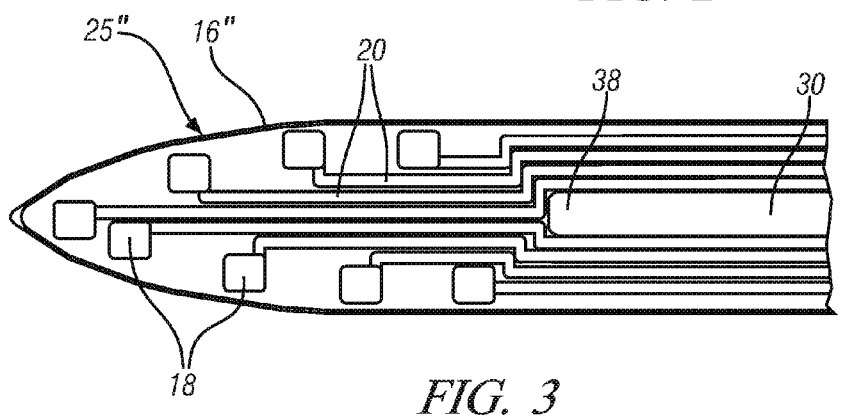
FIG. 3 is a top view of a neural probe tip according to another embodiment.

For example, FIGS. 2 and 3 show embodiments in which waveguide 30 does not extend to the end of tip 16, yet is constructed and oriented on the shank 14 to provide neuron-affecting light at its tip 16. FIG. 2 illustrates an exemplary tip 16' where emitting end 38 of optical waveguide 30 lies within the electrode array region 25' so that some of the electrodes 18 are nearer the probe body than emitting end 38, and other electrodes 18 are further from the probe body than is emitting end 38. FIG. 3 illustrates an exemplary tip 16" where end 38 of optical waveguide 30 lies outside of the electrode array region 25" so that all of the electrodes 18 are further from the probe body than is emitting end 38. The arrangement of FIG. 3 may be useful with shanks or tips having relatively small widths so that the electrode leads 20 can be routed around the end 38 of the waveguide 30, as shown, for access to electrodes 18 at the end of tip 16.

As indicated, the cross-sectional area of the optical waveguide 30 may be only a small fraction of the cross-sectional area of the fiber optic light source 22. For example, a typical fiber optic for use in an optical neural probe may have a clad diameter of about 125 μm, or a cross-sectional area of about 0.012 mm$^2$. Optical waveguide 30 may have a clad width of about 20-30 μm and a clad thickness of about 15-25 μm so that the cross-sectional area may range from about 300-750 μm$^2$. Even at the top end of the range, optical waveguide 30 has a cross-sectional area that is more than an order of magnitude less than the cross-sectional area of the abutting optical fiber, allowing light to be transmitted to the tip of the probe without the bulk of the optical fiber itself extending the length of the probe. As used herein, the term "clad" when placed before a dimensional description such as "clad thickness" or "clad diameter" is meant to describe an overall dimension of the waveguide or fiber optic, including any cladding layers surrounding the optical core.

Light sources other than fiber optic light sources may be coupled to source end 36 of waveguide 30. In one embodiment, illustrated in FIG. 4, the light source 22' is an edge-emitting LED. Neuron-affecting light is emitted from the side of the LED structure, and the emitting region of the LED is comparable in size to the cross-section of the waveguide 30. Various combinations and variations of light sources and fiber optics may also be used to deliver light to the waveguide 30. For example, a probe body-mounted LED may be combined with an optical fiber to deliver light to the waveguide 30.

FIG. 5 illustrates another embodiment where the light source 22" includes one or more LEDs located and mounted directly on the tip 16 of the probe, or otherwise near the recording electrodes 18. The LEDs 22" can be organic LEDs (OLEDs), according to one embodiment. OLED material can be patterned directly at or near the probe tip 16 with transparent electrodes. Separate electrical connections 42 are provided to control the LEDs. It is possible to use several different light sources on a single probe by patterning different OLED materials. For example, LEDs that emit different wavelengths of light (e.g., blue, yellow, and/or non-visible wavelengths) may be used in combination with one another to simultaneously or sequentially provide light at tip 16 that stimulates or silences individual neurons. This arrangement can eliminate the need for a waveguide, optical fibers, and external light sources. Alternatively, patterned OLEDs such as those in FIG. 5 can be used in combination with one or more waveguides and additional light sources for further control over the neuron stimulation and response recording process.

Referring to FIG. 6, a cross-section through the probe body 12 of FIG. 1 is shown. A groove 28 may be included in the probe body 12 to aid in alignment of the fiber optic light source 22 with the waveguide. In this example, a V-shaped groove is illustrated, but the groove 28 may take other forms such as a U-shaped groove or other shape suitable to support and align the core 44 of the optical fiber with the waveguide. In this embodiment, surface 46 represents a <111> plane. Similar types of grooves may be used to align other types of light sources, such as LEDs, with the waveguide. The groove 28 can be made by anisotropic etching of silicon in KOH or by other methods suitable to accurately control the depth and shape of the groove.

Turning now to FIG. 7 for further description of exemplary waveguide 30, a cross-section is shown of the tip 16 of the probe of FIG. 1, again not necessarily to scale. In this embodiment, waveguide 30 includes a core 50, a bottom cladding layer 52, and a top cladding layer 54, where the bottom and top cladding layers 52, 54 are separate from each other. The bottom cladding layer 52 may be an oxide, for example, and the top cladding layer 54 covering the top and sides of the waveguide core 50 may be a polymer layer and/or a dielectric layer. In this particular structure, cladding layer thickness may be limited to approximately 3 μm due to the limitations of conventional fabrication techniques. Additionally, when patterning thicker layers, the resulting surface morphology can limit additional processing on top of the thicker layers. Further, the stress of a thick film is difficult to release in the structure.

FIG. 8 shows another embodiment in which bottom cladding layer 52' is increased in thickness to about 10 μm or more. In order to produce a bottom cladding layer 52' having a thickness above 3 μm, the structure can be modified as shown using special fabrication techniques such as silicon oxide-glass hybrid structure using a glass-melting process. In this structure, in addition to the thickness of bottom cladding layer 52' being 10 μm or more, a stress-free structure can be obtained. In another embodiment, the top cladding material shown in FIGS. 7 and 8 can continue around the bottom of the waveguide core 50 to completely encapsulate the core.

Optical waveguide 30 may include a core 50, as shown in FIGS. 7 and 8, and at least one cladding, whether continuous or including bottom and top layers. Generally, it is preferred that the refractive index of the core material be higher than that of the cladding material or materials to effectively guide light through waveguide 30. The core 50 can be constructed from a polymeric material such as SU-8, or other polymer, or from dielectric materials having a suitable refractive index. One or more additional cladding layers can be included with the waveguide 30 to minimize optical losses. Various materials such as oxides or polymers that have lower refractive indices than that of the core material can be used as the cladding layer or layers, and overall cladding thickness may be increased to a level suitable to minimize optical losses. The optical waveguide 30 may also include one or more optical branches along its length in applications in which it is desirable to stimulate multiple sites simultaneously, or in applications where it is desired to transmit more than one different light source to the tip of the probe.

Figure 9:
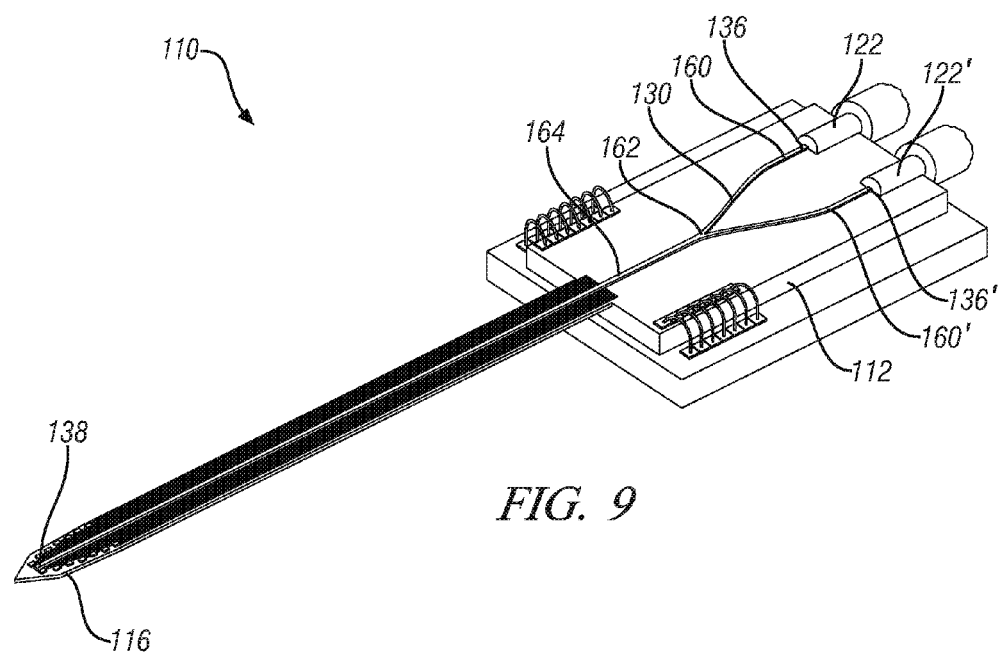
FIG. 9 is an exemplary neural probe including an optical mixer and multiple light sources.

For example, FIG. 9 illustrates exemplary neural probe 110, including all of the same types of elements as exemplary probe 10 of FIG. 1. However, in this embodiment the optical waveguide 130 includes two branches 160, 160', an optical mixer 162, and a shank portion 164. Each of the branches 160, 160' extends from its respective source end 136, 136' and along probe body 112, merging at the optical mixer 162. The shank portion 164 extends from the optical mixer 162 toward the tip 116 of the probe to emitting end 138, as with other waveguides previously presented herein. Waveguide 130 may thus be coupled with two different light sources 122, 122' at source ends 136, 136'. In the embodiment shown, light sources 122, 122' include fiber optics, but other previously described light sources may be used as well, and each may be a different type of light source in some instances. With this construction, neural probe 110 can stimulate or silence neurons at a desired location by emitting light having variable characteristics from the emitting end 138 of the waveguide 130. For example, two different wavelengths of light may be emitted from end 138. This can be accomplished by switching from one light source 122 to the other source 122' and vice versa. If both light sources 122, 122' providing different wavelengths of light are simultaneously illuminated with different pulse modulations when targeting a neuron or neurons, various optical perturbation patterns of the targeted neurons can be expected. The intensity or power of the light may vary by source as well. With multiple light sources, the size of the probe body 112 may increase compared to probes having a single light source such as probe 10 of FIG. 1. This is due to the extra length of waveguide material necessary to gradually merge the two branches 160, 160' at optical mixer 162. While the embodiment shown in FIG. 9 includes two light sources, the number of light sources can be increased to three or more with additional optical mixers used to merge three or more branches into one for extension toward the probe tip. In such embodiments the number of optical mixers can vary as well. A single optical mixer may be capable of merging three or more branches, or multiple mixers may be used to merge individual branches before additionally merging the merged branches.

Figure 10:
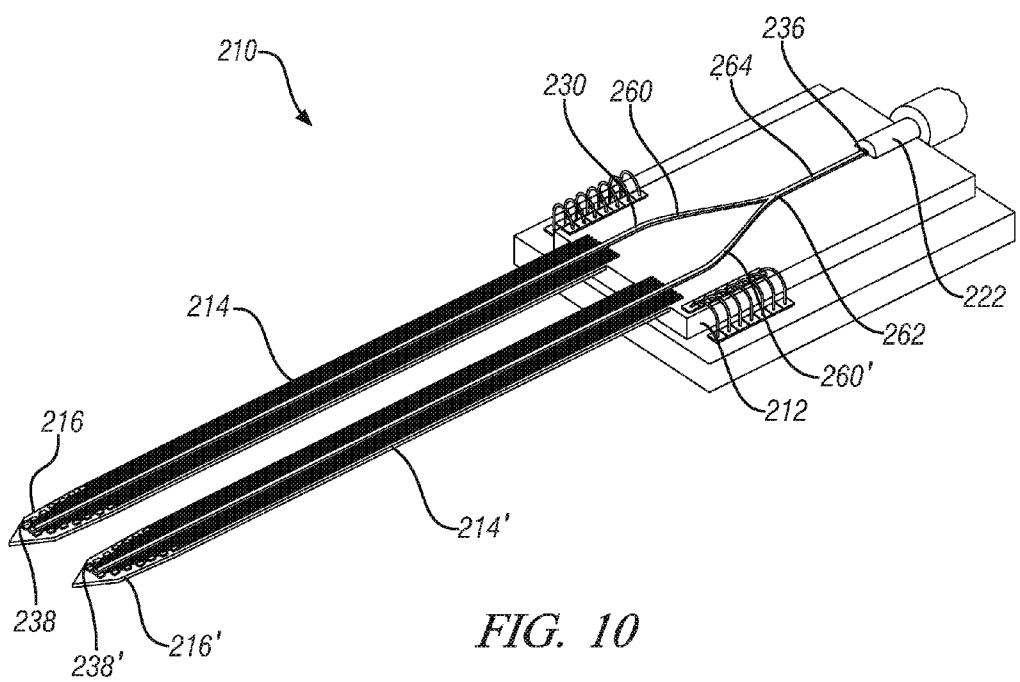
FIG. 10 is an exemplary neural probe including an optical splitter and multiple probe tips.

FIG. 10 illustrates another exemplary neural probe 210, including all of the same types of elements as exemplary probe 10 of FIG. 1. However, in this embodiment the optical waveguide 230 includes two branches 260, 260', an optical splitter 262, and a body portion 264. Body portion 264 extends from source end 236 and along probe body 212 to the optical splitter 262. Each of branches 260, 260' extends away from the optical splitter 262 and gradually away from each other along probe body 212 and toward the two shanks 214, 214'. Each branch further extends along its respective shank 214, 214' toward the two tips 216, 216' of the probe to emitting ends 238, 238'. Waveguide 230 may thus split a single light source 222 and direct the light to more than one emitting end lying along more than one shank or probe tip. In the embodiment shown, light source 222 includes a fiber optic, but other previously described light sources may be used as well. With this construction, neural probe 210 can stimulate or silence neurons at multiple locations simultaneously from a single light source. This can significantly reduce the efforts in packaging. As with the embodiment of FIG. 9, the length of the probe body 212 may increase compared to probes having a single shank such as probe 10 of FIG. 1. This is due to the extra length of waveguide material necessary to gradually separate the two branches 260, 260' as they extend away from optical splitter 262. While the embodiment shown in FIG. 10 includes two branches, the number of branches can be increased to three or more with additional optical splitters, so long as each branch can emit sufficient light at its emitting end to stimulate neurons. Of course, an optical splitter is not necessary to provide neural stimulation to more than one location simultaneously. A neural probe may be constructed that includes more than one shank extending from the probe body. Each shank can support separate waveguides, each having independent light sources, and some shanks may not include a waveguide, but may include other light sources to provide light at their respective tips. In other embodiments, both an optical splitter and an optical mixer can be used to permit use of multiple light sources and to permit stimulation or silencing of neurons from multiple light-emitting sites.

The optical probes disclosed herein are not limited to neuron-affecting light emission only at the tip of the probe. For example, FIG. 11 illustrates a portion of one example of a neural probe 310 including shank 314 that includes more than one electrode array region 325 and 325'. Shank 314 can be used with any of the other various probe bodies, light sources, optical splitters or mixers, etc. disclosed herein. Electrode array region 325 is similar to some previously described electrode arrangements—i.e., it is located at the probe tip 316 with an array of electrodes 318 arranged about the edge or perimeter of the tip 316. Waveguide 330 extends from a source end (not shown) located at the probe body, along shank 314 and toward tip 316, to an emitting end 338. Waveguide 330 in this example does not extend all the way to the end of tip 316. Emitting end 338 lies at or near array region 325 at the end that is nearest the probe body (not shown).

Exemplary shank 314 further includes a second electrode array region 325' located along the shank between the probe body and the probe tip 316. As with other electrode arrays, the array of region 325' includes electrodes 318 disposed near the perimeter or edge of the shank 314, but in this case not at the probe tip 316. In this case, electrodes 318 are located approximately mid-way between the probe body and the probe tip. Of course, in order for the electrodes 318 to receive electrical responses from neurons in their proximity, the neurons must be stimulated, preferably with light energy. To facilitate this, waveguide 330 includes light emitting junction 370.

Referring to FIG. 12, junction 370 is formed where two portions of waveguide 330 meet, the two portions having different cross-sectional areas in this embodiment. More particularly, the larger cross-section portion of waveguide 330 extends from the source end of the waveguide (right side of Figure) and the smaller cross-section portion extends from the emitting (left side of Figure). The different-sized cross-sections form a step or transition at the junction 370. The junction 370 may be located near array region 325', preferably at the end of the array region nearest the probe body and light source as shown. The foregoing description is not to say that the source end and the emitting end of the waveguide are separate pieces that are placed together to form a "junction" in the waveguide; e.g., it may be preferable to pattern the waveguide directly into such a shape having a cross-section that changes along its length. Apart from a step or transition in the width or other cross-sectional shape of the waveguide 330, notches, surface roughening, or other optical features can be provided on the waveguide to effect light emission at different locations along the shank.

As previously described, waveguide 330 typically includes one or more cladding layers to help contain the light travelling through its core. In order to allow junction 370 to emit light, the cladding material or materials are selectively omitted or removed from the junction. In particular, cladding material is selectively omitted or removed, exposing waveguide core material, on portions of the junction facing the array region 325' and its electrodes 318. Cladding material is therefore omitted at transition regions 372 and 374 as indicated. The transition regions may be specifically designed and patterned to emit light in the desired direction, based on the location of the electrodes 318 in array region 325'. In this manner, light from the probe light source is transmitted from the source end and through the larger cross-section portion of waveguide 330 to light emitting junction 370. Because cladding material is not present at or near the transition regions 372 or 374, some of the light is emitted through the transition region surfaces, while the remainder of the light is transmitted through the smaller cross-section portion of the waveguide 330 to the emitting end.

Thus, exemplary probe 310 may be considered to include three light-emitting sites—i.e., one at the probe tip, and two near electrode array region 325' on opposite sides of the waveguide 330—thereby allowing simultaneous neuron stimulation at multiple stimulation zones 375 from a single waveguide along with the collection of electrical responses at corresponding multiple positions along shank 314. Each stimulation zone extends from a light-emitting site, such as emitting end 338 or transition regions 372, 374, located on the shank to various points beyond the outer perimeter 315 of the shank, as shown. Each stimulation zone 375 represents a region from which neural electrical responses to stimulation or silencing are desired to be recorded and/or a region that receives sufficient neuron-affecting light to stimulate or silence neurons. In this embodiment, each stimulation zone 375 partially overlaps one of the array regions 325 or 325', by virtue of the position of each light-emitting site in relation to each stimulation zone.

In this exemplary configuration, and as best shown in FIG. 11, the portion of shank 314 nearest the probe body is wider than the portion of shank 314 nearest the probe tip 316, with the width transition generally corresponding to junction 370 in overall lengthwise position along the shank.

The larger width of the shank on the probe body side of the junction may be necessary to accommodate the electrode leads 320 for the electrodes 318 lying in array region 325'.

Figure 13:
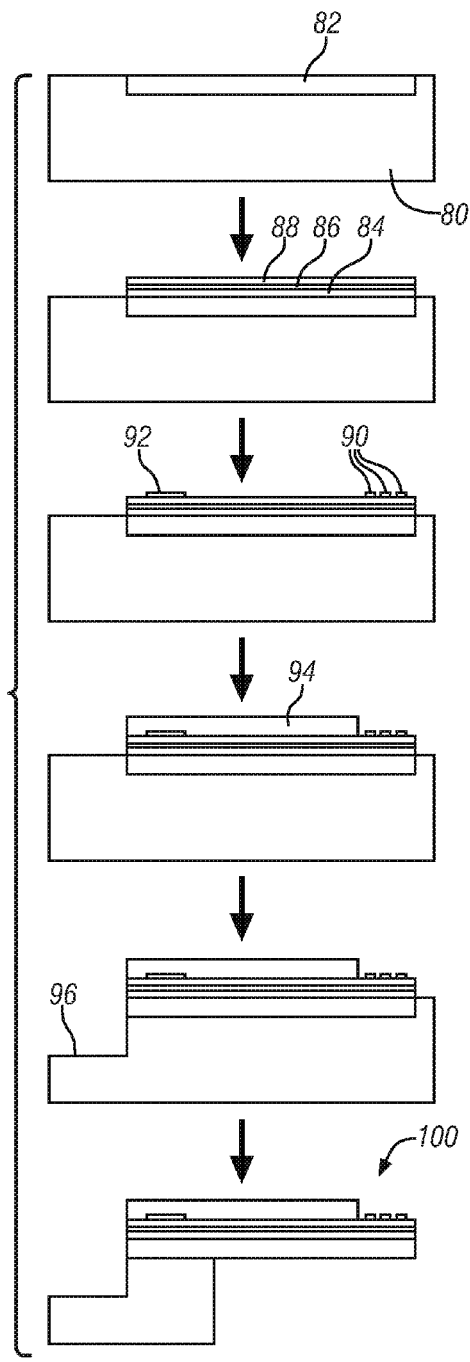
FIG. 13 shows an exemplary method of fabricating a neural probe according to one embodiment.

Exemplary neural probes can be constructed using a variety of techniques. A method according to one embodiment is illustrated in cross-section in FIG. 13, where layer thicknesses are not to scale and are enlarged for clarity. In this method, boron 82 is first diffused into the silicon substrate 80 to form a layer for the probe structure. Then, an oxide/nitride/oxide layer 84 is deposited as a dielectric for stress compensation, and poly-silicon 86 is deposited for interconnections. Next, another dielectric layer 88 is deposited and patterned as a bottom cladding layer for the waveguide. Iridium recording electrodes 90 are deposited and patterned at the desired electrical recording sites, and gold pads 92 are deposited and patterned for electrical connections. Next, an SU-8 optical core 94 is patterned on the cladding oxide layer to produce the optical waveguide core 94. A U-shaped groove 96 is patterned using deep reactive-ion etching (DRIE) for eventually supporting a fiber optic light source at one end of the waveguide (groove 98 is shown in cross-section through the longitudinal center of the U-shape). Finally, the probe 100 is released by wet etching in EDP by using a boron layer as an etch stop layer, as shown in the bottom image of FIG. 13. This method may of course include one or more additional steps, and some steps may be omitted from the process as necessary.

For experimental purposes, an exemplary neural probe was constructed similar to that illustrated in FIG. 1 using the above method. Blue light (475 nm) was used for experimental measurements. The light was transmitted from an external light source to the probe tip through a fiber optic and an optical waveguide. The tip of the experimental probe, more particularly the emitting end of the waveguide, was successfully illuminated. Optical characteristics of the fabricated probe were measured and are shown in FIG. 14. An optical power meter was used to determine coupling losses and waveguide losses using optical waveguides of various lengths. The coupling loss at the interface of the fiber optic and the waveguide was determined to be about −3.7 dB (57%), and the waveguide loss was determined to be about −0.22 dB (4.9%)/mm. An input power of 2.5 mW was used in the experiments. The output power at the tip was measured to be 0.31 mW, which is sufficient for stimulating neurons (E. Boyden et al, "Millisecond-timescale, genetically targeted optical control of neural activity," Nature Neuroscience, vol. 8, pp. 1263-1268, 2005).

Figure 15:
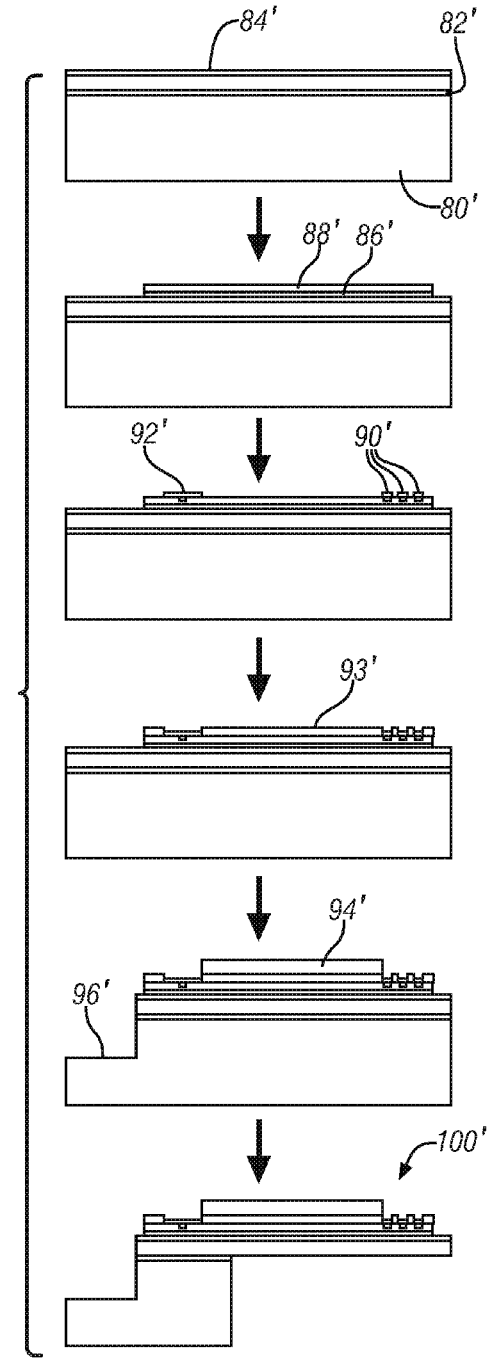
FIG. 15 shows an exemplary method of fabricating a neural probe according to another embodiment.

A method for constructing an exemplary neural probe according to another embodiment is illustrated in cross-section in FIG. 15, where layer thicknesses are not to scale and are enlarged for clarity. Although some element numbers in FIG. 15 correspond with similar elements of FIG. 13, not all numbers necessarily correspond with similar elements between figures. In this method, instead of using a bulk wafer, a silicon-on-insulator (SOI) wafer 80' is used for accurate control of the thickness of the probe shank. SOI wafer 80' includes a buried oxide layer 82'. The thickness of the buried oxide layer is about 2 μm and the thickness of the top Si layer is about 15 μm. The wafer 80' is then thermally oxidized to form an oxide layer 84'. A poly-silicon layer 86' is then deposited and doped with boron for interconnections and may have a thickness of about 500 nm. After patterning the poly-silicon and growing an additional oxide layer 88', iridium and gold are patterned for recording electrodes 90' and bonding pads 92', respectively. After PECVD oxide cladding layer 93' for the bottom of the waveguide is patterned, a layer of SU-8 94' may be patterned for the waveguide. The PECVD oxide layer 93' may be about 3 μm thick, and the SU-8 layer 94' may be about 15 μm thick. One or more grooves 96' to accommodate optical fibers may be etched using DRIE. Finally, the probes may be released by silicon etching from the top and the bottom.

Among the other features of the types of probe fabrication described herein is the ability to form low-profile, integral waveguides. A waveguide formed in this manner may be attached to other underlying probe components continuously along its entire length, can be formed in place in a nearly limitless number of various fixed shapes, and can be formed having cross-sectional dimensions much smaller than a typical optical fiber. For example, as noted, the waveguide core in this example includes SU-8 that may be about 15 μm thick, or about 20-25 μm with top and bottom cladding, while a typical optical fiber may be about 125 μm in diameter with cladding.

For experimental purposes, exemplary neural probes were fabricated similar to those illustrated in FIGS. 9 and 10 using the above method. Each probe that was fabricated included a branched waveguide: one with an optical mixer for use with multiple different light sources, and one with an optical splitter and multiple shanks for use with a single light source and multiple light-emitting tips. The probe with the optical mixer also included a shank and waveguide similar to that shown in FIGS. 11-12, where the probe included more than one electrode array region and the waveguide included a light-emitting junction.

Each of the fabricated probes were fitted with single-mode optical fibers (D=125 μm, Thorlabs, 460HP) as the light source or sources for the respective waveguides. Blue light (473 nm) was used for experimental measurements. Both the probe including the optical mixer and the probe including the optical splitter visually demonstrated successful transmission of the light along the curved waveguides to the end of the 5 mm shanks. In addition, the two additional light-emitting sites at the experimental waveguide light-emitting junction also successfully demonstrated light-emission.

An input power of 6.5 mW was applied from the single-mode optical fiber to the waveguide that included the optical mixer. Output power at all three light-emitting sites was measured. Power at the light-emitting end of the waveguide near the tip of the probe was measured and determined to be 35 μW. Power at each side of the shank at the light-emitting junction was measured and determined to be 15 μW at each side of the shank. With the same power applied to the source end of the waveguide having the optical splitter and two shanks, the power at each of the light-emitting ends after the splitter was measured and determined to be 50 μW. All of these output power levels are sufficient to stimulate neurons.

In addition to demonstrating successful transmission of light through the patterned waveguides, electrical performance of the recording electrodes was also verified by placing each probe tip, non-illuminated, in an electrolyte solution with a reference electrode immersed in the solution. A 1.75 kHz sinusoidal wave was applied to the immersed reference electrode, and electrical signals output from each probe were recorded with a neural data acquisition system (Plexon, Inc.). The output signal from each probe included a corresponding sinusoidal wave of the same frequency.

It is to be understood that the foregoing description is of one or more preferred exemplary embodiments of the invention. The invention is not limited to the particular embodiment(s) disclosed herein, but rather is defined solely by the claims below. Furthermore, the statements contained in the foregoing description relate to particular embodiments and are not to be construed as limitations on the scope of the invention or on the definition of terms used in the claims, except where a term or phrase is expressly defined above. Various other embodiments and various changes and modifications to the disclosed embodiment(s) will become apparent to those skilled in the art. All such other embodiments, changes, and modifications are intended to come within the scope of the appended claims.

As used in this specification and claims, the terms "for example," "for instance," and "such as," and the verbs "comprising," "having," "including," and their other verb forms, when used in conjunction with a listing of one or more components or other items, are each to be construed as open-ended, meaning that the listing is not to be considered as excluding other, additional components or items. Other terms are to be construed using their broadest reasonable meaning unless they are used in a context that requires a different interpretation.

The invention claimed is:

1. A neural probe, comprising:
a probe body;
a shank extending from the probe body to a tip;
a light-emitting diode (LED) light source attached to the tip for providing neuron-affecting light at said tip, wherein the shank is configured to locate the LED light source at a probing depth to target one or more neurons; and
one or more recording electrodes attached to said tip for receiving electrical responses to the neuron-affecting light.

2. A neural probe as defined in claim 1, wherein the LED light source is located near the one or more recording electrodes.

3. A neural probe as defined in claim 2, wherein the one or more recording electrodes comprise a plurality of recording electrodes, and wherein the LED light source is located between at least some of the plurality of recording electrodes.

4. A neural probe as defined in claim 1, comprising a plurality of LED light sources attached to the tip.

5. A neural probe as defined in claim 4, wherein at least two of the plurality of LED light sources are in a staggered configuration.

6. A neural probe as defined in claim 4, wherein one of the LED light sources is located closer to the tip than at least one other of the LED light sources.

7. A neural probe as defined in claim 4, wherein at least two of the plurality of LED light sources each emit a different wavelength of light than the other.

8. A neural probe as defined in claim 7, wherein one wavelength of light stimulates a neuron and another wavelength of light silences a neuron.

9. A neural probe as defined in claim 4, wherein the plurality of LED light sources have separate electrical connections to control the plurality of LED light sources.

10. A neural probe as defined in claim 9, comprising a plurality of recording electrodes having separate electrical connections, and the electrical connections for the plurality of recording electrodes are located on either side of the electrical connections for the LED light sources.

11. A neural probe as defined in claim 1, wherein the LED light source is an edge-emitting LED for providing neuron-affecting light from a side of the LED light source.

12. A neural probe as defined in claim 1, further comprising an optical waveguide extending from a source end at the probe body to an emitting end near said tip, wherein a second light source is in communication with the source end and the neuron-affecting light is provided at the tip by the emitting end and the LED light source.

13. A neural probe as defined in claim 12, wherein the second light source comprises a fiber optic having a first end in communication with an external light source and a second end abutting the source end of the optical waveguide.

14. A neural probe as defined in claim 12, wherein the second light source comprises an LED light source mounted adjacent the source end of the optical waveguide.

15. A neural probe as defined in claim 1, wherein the LED light source is an organic light-emitting diode (OLED) light source.

16. A neural probe as defined in claim 1, further comprising a second shank extending from the probe body to a second tip and a second light-emitting diode (LED) light source attached to the second tip for providing neuron-affecting light at said second tip.

17. A neural probe as defined in claim 1, wherein the LED light source has an electrical connection patterned on the shank.

18. A neural probe, comprising:
a probe body;
a shank extending from the probe body to a tip;
a light-emitting diode (LED) light source patterned on the shank for providing neuron-affecting light; and
one or more recording electrodes attached to said tip for receiving electrical responses to the neuron-affecting light.

19. A neural probe as defined in claim 18, wherein the patterned LED light source includes a transparent electrode.

20. A neural probe as defined in claim 18, further comprising at least one other LED light source patterned on the shank, and wherein the LED light sources are organic light-emitting diode (OLED) light sources patterned from different OLED materials.

21. A neural probe as defined in claim 18, wherein the one or more recording electrodes have an electrical connection and the LED light source, the recording electrodes, and the electrical connections for the one or more recording electrodes are patterned on an outer surface of the shank.

22. A neural probe, comprising:
a probe body;
a shank extending from the probe body to a tip and having an outer perimeter;
a light-emitting diode (LED) light source patterned at the tip for providing neuron-affecting light at said tip; and
a plurality of recording electrodes for receiving electrical responses to the neuron-affecting light, wherein the plurality of recording electrodes are attached to said tip such that they are closer to the outer perimeter of the shank than the LED light source.

23. A neural probe as defined in claim 18, comprising a plurality of LED light sources patterned on the shank.

* * * * *